(12) United States Patent
Aoyama

(10) Patent No.: US 8,710,249 B2
(45) Date of Patent: Apr. 29, 2014

(54) MALTOL ETHER PROCESSES AND INTERMEDIATES

(75) Inventor: Yasunori Aoyama, Amagasaki (JP)

(73) Assignee: Shionogi & Co., Ltd., Osaka (JP)

( * ) Notice: Subject to any disclaimer, the term of this patent is extended or adjusted under 35 U.S.C. 154(b) by 264 days.

(21) Appl. No.: 13/133,481

(22) PCT Filed: Dec. 8, 2009

(86) PCT No.: PCT/IB2009/007678
§ 371 (c)(1),
(2), (4) Date: Jun. 8, 2011

(87) PCT Pub. No.: WO2010/067176
PCT Pub. Date: Jun. 17, 2010

(65) Prior Publication Data
US 2011/0245516 A1    Oct. 6, 2011

Related U.S. Application Data

(60) Provisional application No. 61/193,635, filed on Dec. 11, 2008.

(51) Int. Cl.
*C07D 309/40* (2006.01)

(52) U.S. Cl.
USPC .......................... 549/417; 549/418

(58) Field of Classification Search
USPC .................................. 549/417, 418
See application file for complete search history.

(56) References Cited

U.S. PATENT DOCUMENTS

2011/0183940 A1    7/2011    Johns et al.

FOREIGN PATENT DOCUMENTS

WO    2006/116764    11/2006
WO    2010/011814    1/2010

OTHER PUBLICATIONS

International Search Report issued Mar. 9, 2010 in International (PCT) Application No. PCT/IB2009/007678 along with the Written Opinion.

M. Ghandi et al., "A Novel Method for the Synthesis of Formyl and Hydroxymethyl Derivatives of *4H*-Pyran-4-One", Organic Preparations and Procedures International, vol. 34, No. 5, pp. 525-530, 2002.

S. Kukolja et al., "Studies and 4-Pyrones and 4-Pyridones. II. The Preparation and Rearrangement of 3-Allyloxy-4-pyrone", Croatica Chemica Acta, vol. 33, pp. 229-233, 1961.

European Search Opinion issued in corresponding European Application No. 09 831 529.4, (May 29, 2013).

*Primary Examiner* — B Dentz

(74) *Attorney, Agent, or Firm* — Wenderoth, Lind & Ponack, L.L.P.

(57) ABSTRACT

Novel processes and intermediates are provided according to the general reaction scheme: Formula I, II, III, IV (I), (II), (III), (IV) utilizing a ruthenium catalyst in an oxidative cleavage of the triene 4 whereby an aldehyde may be produced and optionally taken on to a carboxylic acid 5: Formula V (V)

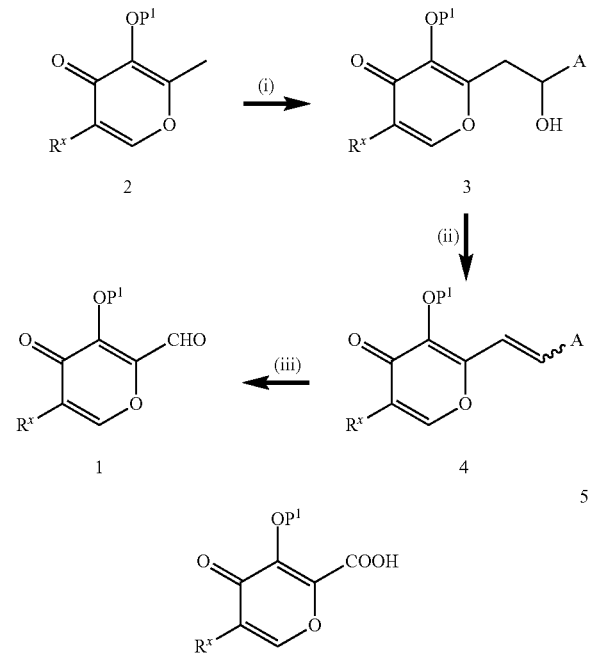

9 Claims, No Drawings

MALTOL ETHER PROCESSES AND INTERMEDIATES

This application is a U.S. national stage of International Application No. PCT/IB2009/007678 filed Dec. 8, 2009, which claims the benefit of U.S. provisional application Ser. No. 61/193,635 filed Dec. 11, 2008.

FIELD OF THE INVENTION

The present invention generally relates to synthetic organic reaction sequences that provide a key intermediate in the production of medicinal compounds useful as HIV integrase inhibitors in the treatment of viral diseases, in particular, the treatment of HIV infection.

BACKGROUND OF THE INVENTION

WO 2006/116764 published Nov. 2, 2006 to Shionogi & Co. Ltd of Osaka, Japan teaches various polycyclic carbamoylpyridone compounds having HIV integrase activity. At page 113, there is described a reaction sequence as follows:

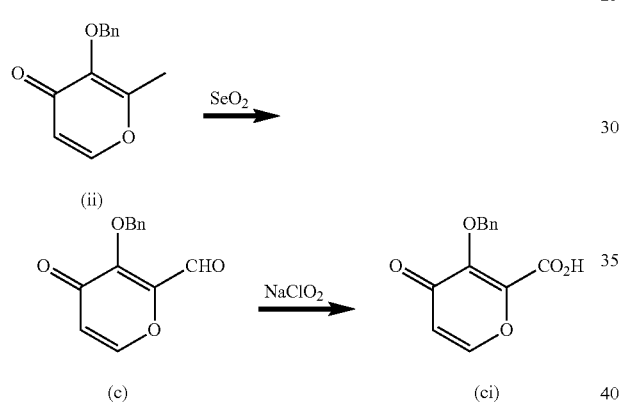

whereby selenium dioxide is added to a solution of the benzyl ether of maltol designated above as (ii), heating the mixture to 160° C., recovering aldehyde (c) and then oxidizing the aldehyde with sodium chlorate to yield carboxylic acid (ci).

SUMMARY OF THE INVENTION

There is provided a process for preparing an aldehyde of the following formula 1 from the corresponding methyl compound of formula 2 without the use of a highly toxic selenium reagent:

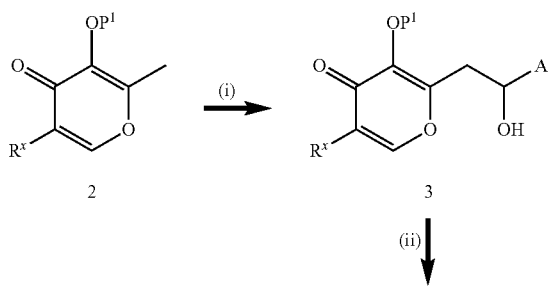

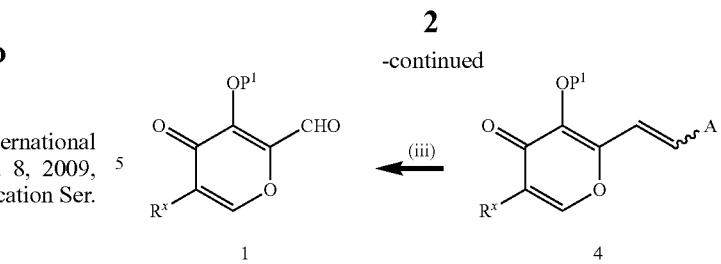

The process comprises the steps of:
i) aldol reaction of 2 with an aldehyde of formula A-CHO to produce the alcohol 3;
ii) elimination reaction of the alcohol 3 to produce the triene 4; and
iii) oxidative cleavage of the triene 4 to produce the aldehyde of formula 1.

DETAILED DESCRIPTION OF THE INVENTION

The present invention features a process of producing an aldehyde of the formula 1:

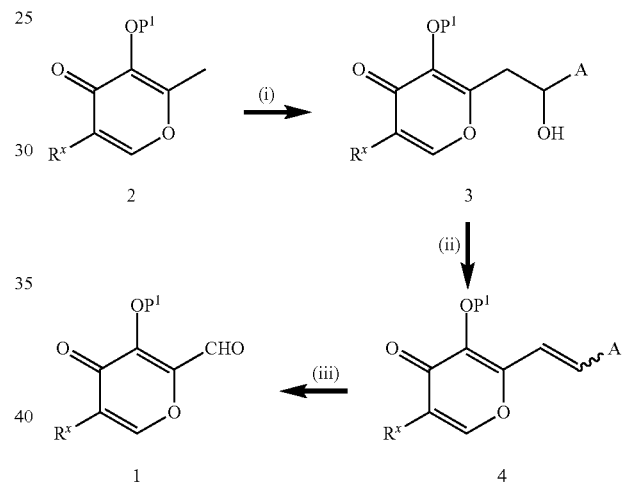

wherein
$P^1$ is hydrogen or a hydroxyl protecting group;
$R^x$ is hydrogen, halo, or $R^2$—X—$NR^1$—C(O)—;
$R^1$ is hydrogen or lower alkyl;
X is a single bond, a heteroatom group selected from O, S, SO, $SO_2$, and NH or loweralkylene or lowerlalkylene wherein each may be intervened by a heteroatom;
$R^2$ is optionally substituted aryl; and
A is alkyl or aryl,
which comprises the steps of:
i) reacting pyrone 2 with an aldehyde of formula A-CHO to produce the alcohol 3;
ii) reacting the alcohol 3 with a dehydrating reagent to produce the triene 4; and
iii) reacting the triene 4 with an oxidating reagent to produce the aldehyde of formula 1.

The present invention also features a process as described above, wherein $P^1$ and $R^x$ are hydrogen, A is phenyl and the wavy line bond in triene 4 is a trans bond. Another preferable aspect is that $P^1$ is hydroxyl protecting group, $R^x$ is hydrogen, A is phenyl and the wavy line bond in triene 4 is a trans bond.

The present invention also features a process as described above, wherein step (i) is conducted in the presence of a base.

The present invention also features a process as described above, wherein step (ii) is conducted in the presence of base.

The present invention also features a process as described above, wherein the oxidating reagent is preferably ruthenium reagent. The ruthenium reagent is preferably ruthenium tetroxide generated in situ.

The term "lower alkyl", alone or in combination with any other term, refers to a straight-chain or branched-chain saturated aliphatic hydrocarbon radical containing 1 to 6 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like. The term "lower alkyl" is preferably C1-C4 alkyl.

The term "lower alkylene" refers to a straight or branched chain divalent hydrocarbon radical, preferably having from one to six carbon atoms, unless otherwise defined. Examples of "alkylene" as used herein include, but are not limited to, methylene, ethylene, propylene, butylene, isobutylene and the like. The term "lower alkylene" is preferably C1-C4 alkylene.

The term "lower alkenylene" refers to a straight or branched chain divalent hydrocarbon radical, one or two carbon-carbon double bonds. The term "lower alkenylene" is preferably C2-C4 alkylene The term "halo" or "halogen" refers fluorine (F), chlorine (Cl), bromine (Br), or iodine (I).

The term "aryl" alone or in combination with any other term, refers to a carbocyclic aromatic moiety (such as phenyl or naphthyl) containing 6 carbon atoms, and more preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. The term "aralkyl" refers to an alkyl group substituted by an aryl. Examples of aralkyl groups include, but are not limited to, benzyl and phenethyl. The term "aryl" is preferably phenyl.

Optional substituents on aryl are one or two group selected from hydroxy, halogen, amino and lower alkyl.

"Hydroxyl Protecting group" may be selected from groups known to those skilled in the art, including protecting groups disclosed in Greene, Theodora W.; Wuts, Peter G. M. Protective Groups in Organic Synthesis. 2nd Ed. (1991), 473 pp. or Kocienski, Philip J. Protecting Groups. 3rd Ed. 2005, (2005), 679 pp. Preferred is alkyl or arylalkyl (e.g., benzyl).

The starting material of the invention process may be a pyrone of the following formula 2:

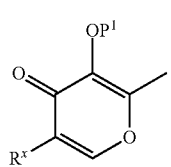

2 wherein

P$^1$ is hydrogen or a hydroxyl protecting group;

R$^x$ is hydrogen, halo such as Br, or R$^2$—X—NR$^1$—C(O)—;

R$^1$ is hydrogen or lower alkyl;

X is a single bond, a heteroatom group selected from O, S, SO, SO$_2$, and NH or loweralkylene or lowerlalkylene wherein each may be intervened by a heteroatom; and R$^2$ is optionally substituted aryl.

In one of preferable embodiments, P$^1$ is hydroxyl protecting group such as arylalkyl (e.g., benzyl (: Bn)), R$^x$ is hydrogen.

For the aldehyde A-CHO used in step (i) to produce the alcohol 3, A may be an alkyl or aryl group such as methyl, ethyl, n-propyl, isopropyl, n-butyl, isobutyl, sec-butyl, tert-butyl, pentyl, isoamyl, n-hexyl, phenyl or substituted phenyl and preferred is phenyl:

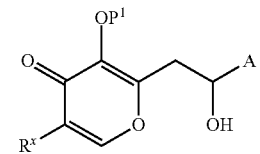

3

The step (i) is conducted preferably in the presence of a base such as LiHMDS, NaHMDS, KHMDS, LDA, KDA, NaOEt or KOtBu and preferred is LiHMDS.

The reaction is conducted at about −100° C. to under ice-cooling and preferably at −80° C. to −50° C.

The reaction solvent is such as THF, DME, diglyme, TBME, or CPME and preferably THF.

The product of the elimination step (ii) is the triene 4 wherein the wavy bond depicted is indicative of either a cis or trans configuration, preferably trans being the expected product:

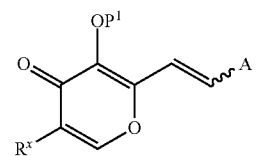

4

The step (ii) is conducted preferably in the presence of a base such as Et$_3$N, iPr$_2$NEt, or DBU. More preferably, compound 3 may be activated in advance by an activating reagent such as mesylating (e.g., MsCl), tosylating reagent (e.g., TsCl) or chlorinating (e.g., SOCl$_2$).

The reaction temperature is preferably 0° C. to 100° C., preferably 0° C. to 40° C., more preferably around room temperature.

The reaction solvent is preferably THF, DME, DMF, DMA, NMP or MeCN, and more preferably THF.

The catalytic system used in step (iii) to produce the aldehyde 1 may be oxidating reagent, preferably ruthenium reagent. The ruthenium reagent is preferably ruthenium tetroxide, which may be generated in situ from RuCl$_3$/NaIO$_4$ or RuCl$_3$/HIO$_4$.

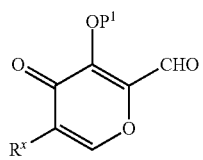

1

In the above formulas 3, 4 and 1, the moieties $P^1$ and $R^x$ are as defined for pyrone 2 and A in triene 4 is as defined for alcohol 3.

A further aspect of the invention is the step of oxidizing the aldehyde of formula 1 to yield the carboxylic acid of formula 5 in a step (iv):

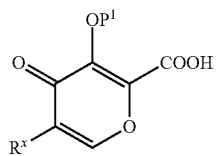

5 wherein $P^1$ and $R^x$ are as defined above for the pyrone of formula 2.

In step (iv), the oxidizing reagent used in step (iv) is preferably sodium chlorite or sodium hypochlorite.

The reaction temperature is preferably 0° C. to 100° C., preferably 0° C. to 40° C., more preferably 5° C. to 20° C.

The reaction solvent is preferably DMF, MeCN, AcOEt, water or a mixture thereof etc.

Also part of the present invention are novel intermediates such as those novel compounds of formulae 3 and 4.

The present invention also features an alcohol of the following formula 3:

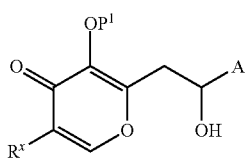

3 wherein
  $P^1$ is hydrogen or a hydroxyl protecting group;
  $R^x$ is hydrogen, halo, or $R^2$—X—$NR^1$—C(O)—;
  $R^1$ is hydrogen or lower alkyl;
  X is a single bond, a heteroatom group selected from O, S, SO, $SO_2$, and NH or loweralkylene or lowerlalkylene wherein each may be intervened by a heteroatom;
  $R^2$ is optionally substituted aryl; and
  A may be an alkyl or aryl group such as methyl, ethyl, n-propyl, isopropyl, n-butyl, isobutyl, sec-butyl, tert-butyl, pentyl, isoamyl, n-hexyl, phenyl or substituted phenyl and preferred is phenyl:

An alcohol as described above, wherein $P^1$ and $R^x$ are hydrogen, and A is phenyl is included within the invention.

The present invention features a triene of the following formula 4:

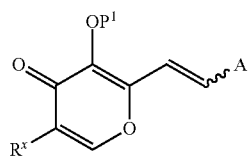

4 wherein
  $P^1$ is hydrogen or a hydroxyl protecting group;
  $R^x$ is hydrogen, halo, or $R^2$—X—$NR^1$—C(O)—;
  $R^1$ is hydrogen or lower alkyl;
  X is a single bond, a heteroatom group selected from O, S, SO, $SO_2$, and NH or loweralkylene or lowerlalkylene wherein each may be intervened by a heteroatom;
  $R^2$ is optionally substituted aryl; and
  A may be an alkyl or aryl group such as methyl, ethyl, n-propyl, isopropyl, n-butyl, isobutyl, sec-butyl, tert-butyl, pentyl, isoamyl, n-hexyl, phenyl or substituted phenyl and preferred is phenyl: and
  the wavy line bond is either cis or trans.

In the triene as described above, $P^1$ and $R^x$ may be hydrogen, A may be phenyl and the wavy line bond may be trans.

The present invention features a process for producing a carboxylic acid of the following formula 5:

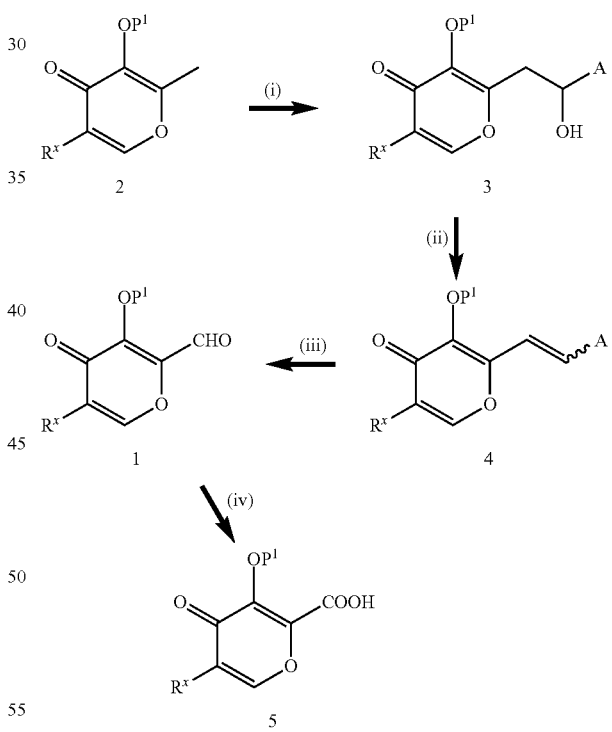

wherein
  $P^1$ is hydrogen or a hydroxyl protecting group;
  $R^x$ is hydrogen, halo, or $R^2$—X—$NR^1$—C(O)—;
  $R^1$ is hydrogen or lower alkyl;
  X is a single bond, a heteroatom group selected from O, S, SO, $SO_2$, and NH or loweralkylene or lowerlalkylene wherein each may be intervened by a heteroatom;
  $R^2$ is optionally substituted aryl; and
  A may be an alkyl or aryl group such as methyl, ethyl, n-propyl, isopropyl, n-butyl, isobutyl, sec-butyl, tert-butyl, pentyl, isoamyl, n-hexyl, phenyl or substituted phenyl and preferred is phenyl:

which comprises the steps of:
i) reacting pyrone 2 with an aldehyde of formula A-CHO to produce the alcohol 3;
ii) reacting the alcohol 3 with a dehydrating reagent to produce the triene 4;
iii) reacting the triene 4 with a ruthenium reagent to produce the aldehyde of formula 1: and
iv) oxidizing the aldhyde of formula 1 to produce the carboxylic acid of formula 5.

EXAMPLES

In this specification, each abbreviations represent as follows.
THF: tetrahydrofuran
DME: dimethoxyethan
diglyme: ethyleneglycol dimethyl ether
DMF: N,N-dimethylformamide
DMA: N,N-dimethylacetamide
TBME: t-butyl methyl ether
CPME: cyclopentyl methyl ether
LiHMDS: lithium hexamethyldisilazane
NaHMDS: sodium hexamethyldisilazane
KHMDS: potassium hexamethyldisilazane
LDA: lithium diisopropylamide
KDA: potassium diisopropylamide
NaOEt: sodium ethoxide
NaOtBu: sodium tert-butoxide
KOtBu: potassium tert-butoxide
Me: methyl
Bn: benzyl
Ph: phenyl
Et₃N: triethylamine
MsCl: methanesulfonyl chrolide
TsCl: toluenesulfonyl chrolide
DBU: 1,8-diazabicyclo[5.4.0]undec-7-ene
TEMPO: 2,2,6,6-tetramethylpiperidine 1-oxyl
NMP: N-methylpyrrolidone
AcOEt: ethyl acetate The reaction steps are shown below.

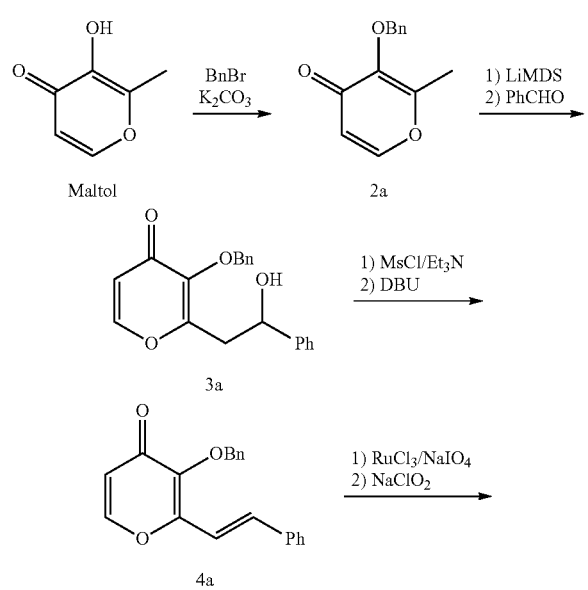

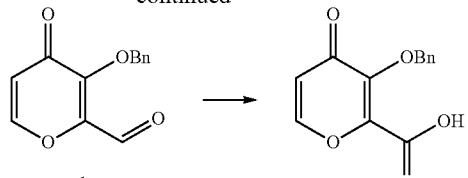

Reference Example A

Page 113 of WO 2006/116764 going from 2 to 100 to 101 with the narratives 1) and 2) of page 113.

Example A

Maltol to Benzylmaltol 2a
Maltol: 2000 g
BnBr: [MW=171.04, d=1.444] 2848.2 g (1.05 eq)
K₂CO₃ [MW=138.21] 2630.3 g (1.2 eq)
MeCN 14 L 7V To the solution of 2000 g of Maltol in MeCN (14 L) was added BnBr (2848.2 g) and K₂CO₃ (2630.3 g) at room temperature. (around 23° C.)

After addition of reagent, the temperature of the reaction mixture was getting high.

This reaction mixture was kept at 80° C. for 5 hr and then cooled down to room temperature. The reaction mixture was filtered and washed with MeCN (3 L, 1 L, 1 L). Filtration was concentrated and added THF 2 L and concentrated again. (check the KF 1.33%).

THF 1.5 L was added to the residue and concentrate again. (KF=0.135%)

The residue 2a: 3648 g

Example 1.1

Benzylmaltol 2a to 3-Benzyloxy-2-(2-hydroxy-2-phenyl-ethyl)-pyran-4-one 3a 2a: 2300 g 1.0M LiHMDS in THF: 12.5 L (1.25 eq)
PhCHO [MW=106.12]: 1273.4 g (1.2 eq)

To the solution of 2a (2300 g) in THF 14.9 L was cooled down to −60° C. and added LiHMDS 12.5 L and PhCHO (1273.4 g) in THF 2.0 L. (temp: −60° C.). The reaction mixture was stirred for 1 hr at −60° C.

This reaction mixture was poured into ice water 19.5 L (9V) and conc. HCl 2.9 L (1.34V) and AcOEt 10.8 L (5V). The organic layer was washed with H₂O 6.3 L twice and concentrated and toluene was added 4 L and concentrated again. To this residue was added toluene 4 L and cooled down to 0° C. The suspension was filterated and washed with toluene 2 L. 2326 g of 3a was obtained (72% from Maltol).

Example 1.2

3-Benzyloxy-2-(2-hydroxy-2-phenyl-ethyl)-pyran-4-one 3a to 3-Benzyloxy-2-((E)-styryl)-pyran-4-one 4a

| | |
|---|---|
| 3a [MW = 322.35] | 882.3 g |
| THF | 8.8 L (10 V) |
| TEA [MW = 101.19] | 415.5 g (1.5 eq) |
| MsCl [MW = 114.54] | 407.5 g (1.3 eq) |
| NMP | 440 mL |
| DBU [MW = 152.24] | 1166.8 g (2.8 eq) |

To the solution of 3a and TEA in THF (8.8 L) was added dropwise MsCl at room temperature. (22.8° C.-29° C.) and stirred for 30 min. (TLC check). After addition of NMP to this reaction mixture, DBU was added dropwise over 1 hr. (25-27° C.), followed by dropwise addition of 1.76 L solution: 1:4 mixture of 62% $H_2SO_4$:13% NaCl. (16-27° C.) The reaction mixture was extracted with AcOEt, and the extracts was washed with 2% $Na_2SO_3$aq. The organic layer was evaporated in vaccuo and 5V of toluene was added, again evaporated. Evaporation was stopped when volume was reduced to ca 2V. After crystalline appears (seeding is preferred), 6V of hexane was added and cooled with an ice bath. Crystalline solid was collected by filtration and washed with 2V of hexane. A second lot was conducted and 1559.6 g of compound 4a was obtained (93.6% yield).

Example 1.3

3-Benzyloxy-2-((E)-styryl)-pyran-4-one 4a to 3-Benzyloxy-4-oxo-4H-pyran-2-carbaldehyde 1a

| | |
|---|---|
| 4a [MW = 304.34] | 870.7 g |
| $RuCl_3$, $nH_2O$ [MW = 207.43] | 13.06 g (2.2 mol %) |
| $NaIO_4$ [MW = 213.88] | 2.45 kg (4 eq) |
| $CH_3CN$ | 2.6 L (3 V) |
| AcOEt | 2.6 L (3 V) |
| $H_2O$ | 2.6 L (3 V) |

To the ice-cooled stirring mixture of 4a, $CH_3CN$, AcOEt, and $H_2O$ was added $RuCl_3$,$nH_2O$. Following addition of $NaIO_4$ powder was conducted portionwisely during 4 hours. (6-18° C.) to provide a mixture of 1a.

Example 1.4

3-Benzyloxy-4-oxo-4H-pyran-2-carbaldehyde 1a to 3-Benzyloxy-4-oxo-4H-pyran-2-carboxylic acid 5a

| | |
|---|---|
| $NaClO_2$ [MW = 90.44] | 776 g (3 eq) |

After stirring the reaction mixture from Example 1.3 for 2 hours, $NaClO_2$ powder was added during 2 hours. Temperature was kept below 16° C. during this addition and the mixture was stirred for 1 hour after addition. Insoluble was filtered off and washed with AcOEt. The filtrate was diluted with 50% $Na_2S_2O_3$aq. and acidified with HCl to pH=2 (ca.). Organic layer was separated and concentrated in vaccuo. 2 L of toluene was added to the residue and about 1 L was evaporated off. The rest of the solution was cooled with ice bath and crystalline solid was collected by filtration. A second lot was conducted and gave 688 g of compound of formula 5a where $P^1$ and $R^x$ are both H in 48.8% yield.

Example 1.5

Another Method to Yield Compound 5a from Compound 4a

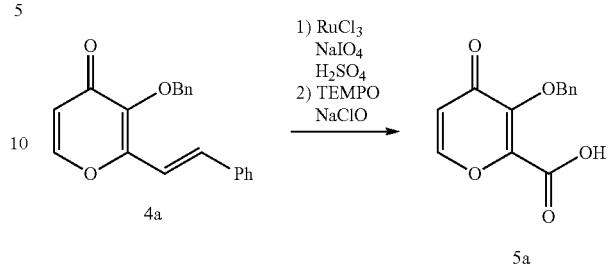

3-Benzyloxy-2-((E)-styryl)-pyran-4-one 4a to 3-Benzyloxy-4-oxo-4H-pyran-2-carboxylic acid 5a

| | |
|---|---|
| 4a [MW = 304.34] | 10.0 g (32.86 mmol) |
| $RuCl_3$, $nH_2O$ [MW = 207.43] | 13.0 mg (0.2 mol %) |
| $NaIO_4$ [MW = 213.88] | 15.5 g (2.2 eq) |
| $H_2SO_4$ [MW = 98.08] | 7.2 g (2.2 eq) |
| MeCN | 95 mL |
| $H_2O$ | 10 mL |
| 5% $NaHCO_3$ | 60 mL |
| TEMPO [MW = 156.25] | 257 mg (5 mol %) |
| NaClO solution | 25.9 g |

To a mixture of 10.0 g of compound 4a and 13.6 mg of $RuCl_3$.$nH_2O$ in 95 mL of MeCN and 10 mL of water, mixture of 155 mL of water, 7.2 g of hydrosulfuric acid, and 15.5 g of $NaIO_4$ was added for 2.5 h at 20° C. After aging for 1 h, organic and aqueous layers were separated and aqueous layer was extracted by 30 mL of AcOEt. Aqueous layer was extracted again by 30 mL of ethyl acetate and organic layers were combined. 6 mL of 5% $NaHSO_3$ solution was added to the combined organic layer and the layers were separated. The organic layer was adjusted to pH 6.0 by adding 4.0 g of 2M NaOH solution and the aqueous layer was separated. After 60 mL of 5% $NaHCO_3$ solution and 257 mg of TEMPO was added, 25.9 g of NaClO solution was added to the reaction mixture at 25° C. for 1 h and stirred for 30 min to check the reaction was finished. After the layers were separated, 42.5 mL of 5% $Na_2SO_3$ solution and 30 mL of AcOEt were added and separated. The aqueous layer was extracted by 30 mL of AcOEt and separated. 12% $H_2SO_4$ was added to the reaction mixture at 20° C. for 1 h and the mixture was cooled to 5° C. After the mixture was stirred for 30 min, the mixture was filtered, washed with 30 mL of water twice and dried to provide 5.7 g of compound 5a (70% yield) as a crystal.
Compound 5a:
$^1$H NMR (300 MHz, $CDCl_3$) δ 7.78 (d, J=5.7 Hz, 1H), 7.54-7.46 (m, 2H), 7.40-7.26 (m, 3H), 6.48 (d, J=5.7 Hz, 1H), 5.6 (brs, 1H), 5.31 (s, 2H).

What is claimed is:
1. A process of producing an aldehyde of formula 1,

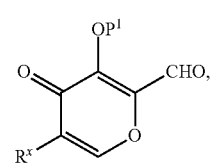

which comprises the steps of:
(i) reacting a pyrone of formula 2 with an aldehyde of formula A-CHO to produce an alcohol of formula 3;
(ii) reacting the alcohol of the formula 3 with a dehydrating reagent to produce a triene of formula 4; and
(iii) reacting the triene of the formula 4 with an oxidating reagent to produce the aldehyde of the formula 1,

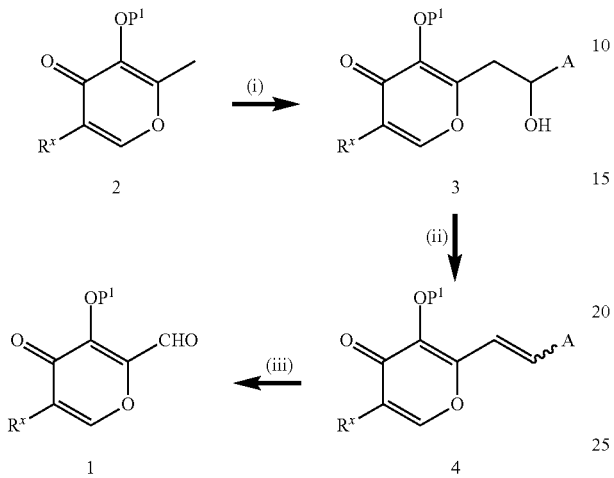

wherein:
P$^1$ is hydrogen or a hydroxyl protecting group;
R$^x$ is halogen or R$^2$—X—NR$^1$—C(O)—;
R$^1$ is hydrogen or lower alkyl;
X is a single bond, a heteroatom group selected from the group consisting of O, S, SO, SO$_2$ and NH, a loweralkylene or a loweralkylene wherein each alkyl may be intervened by a heteroatom;
R$^2$ is optionally substituted aryl; and
A is aryl.

2. The process of claim 1, wherein step (i) is reacted in the presence of a base.

3. The process of claim 1, wherein step (ii) is reacted in the presence of a base.

4. The process of claim 1, wherein the oxidating reagent is a ruthenium reagent.

5. The process of claim 1, wherein the ruthenium reagent is ruthenium tetroxide generated in situ.

6. An alcohol of the following formula 3:

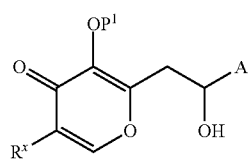

wherein:
P$^1$ is hydrogen or a hydroxyl protecting group;
R$^x$ is halogen or R$^2$—X—NR$^1$—C(O)—;
R$^1$ is hydrogen or lower alkyl;
X is a single bond, a heteroatom group selected from the group consisting of O, S, SO, SO$_2$ and NH, a loweralkylene or a loweralkylene wherein each alkyl may be intervened by a heteroatom;
R$^2$ is optionally substituted aryl; and
A is aryl.

7. A triene of the following formula 4:

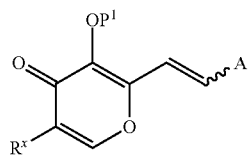

wherein:
P$^1$ is hydrogen or a hydroxyl protecting group;
R$^x$ is halogen or R$^2$—X—NR$^1$—C(O)—;
R$^1$ is hydrogen or lower alkyl;
X is a single bond, a heteroatom group selected from the group consisting of O, S, SO, SO$_2$ and NH, a loweralkylene or lowerlalkylene a loweralkylene wherein each alkyl may be intervened by a heteroatom;
R$^2$ is optionally substituted aryl;
A is aryl; and
the wavy line bond is either cis or trans.

8. A process of producing a carboxylic acid of formula 5,

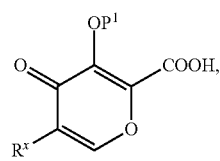

which comprises the steps of:
(i) reacting a pyrone of formula 2 with an aldehyde of formula A-CHO to produce an alcohol of formula 3;
(ii) reacting the alcohol of the formula 3 with a dehydrating reagent to produce a triene of formula 4;
(iii) reacting the triene of the formula 4 with an oxidating reagent to produce an aldehyde of formula 1: and
(iv) oxidizing the aldehyde of the formula 1 to produce the carboxylic acid of the formula 5,

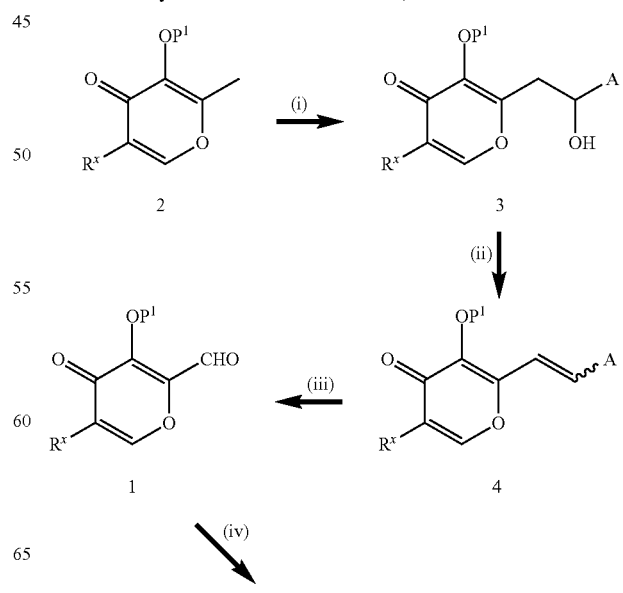

-continued

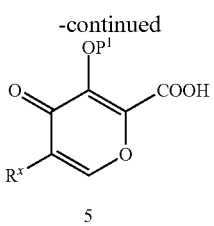

5 wherein:
P¹ is hydrogen or a hydroxyl protecting group;
R$^x$ is halogen or R²—X—NR¹—C(O)—;
R¹ is hydrogen or lower alkyl;
X is a single bond, a heteroatom group selected from the group consisting of O, S, SO, SO₂—and NH, a loweralkylene or lowerlalkylene a loweralkylene wherein each alkyl may be intervened by a heteroatom;
R² is optionally substituted aryl; and
A is aryl.

9. A process of producing a carboxylic acid of formula 5,

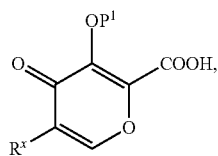

which comprises the steps of:
(iii) reacting a triene of formula 4 with an oxidating reagent to produce an aldehyde of formula 1; and
(iv) oxidizing the aldehyde of the formula 1 to produce the carboxylic acid of the formula 5,

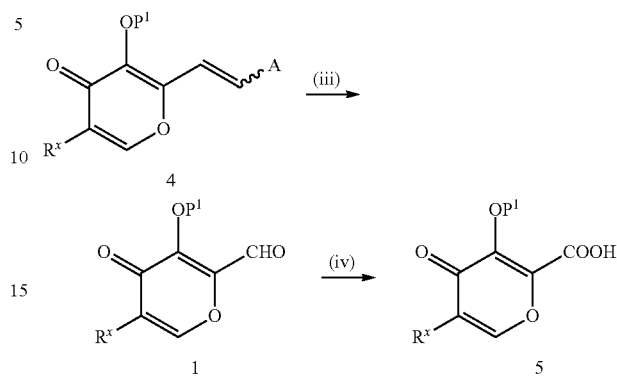

wherein:
P¹ is hydrogen or a hydroxyl protecting group;
R$^x$ is halogen or R²—X—NR¹—C(O)—;
R¹ is hydrogen or lower alkyl;
X is a single bond, a heteroatom group selected from the group consisting of O, S, SO, SO₂ and NH, a loweralkylene or a loweralkylene wherein each alkyl may be intervened by a heteroatom;
R² is optionally substituted aryl; and
A is aryl.

* * * * *